US009116084B2

(12) United States Patent
Hill et al.

(10) Patent No.: US 9,116,084 B2
(45) Date of Patent: Aug. 25, 2015

(54) METHOD AND SAMPLING SYSTEM FOR TAKING SAMPLE FROM THE ATMOSPHERE IN THE REACTOR CONTAINMENT OF A NUCLEAR PLANT

(75) Inventors: Axel Hill, Stockstadt (DE); Bernd Eckardt, Bruchköbel (DE)

(73) Assignee: Areva GmbH, Erlangen (DE)

( * ) Notice: Subject to any disclaimer, the term of this patent is extended or adjusted under 35 U.S.C. 154(b) by 872 days.

(21) Appl. No.: 11/786,805

(22) Filed: Apr. 13, 2007

(65) Prior Publication Data

US 2008/0175345 A1 Jul. 24, 2008

Related U.S. Application Data

(63) Continuation of application No. PCT/EP2005/011024, filed on Oct. 13, 2005.

(30) Foreign Application Priority Data

Oct. 14, 2004 (DE) .......................... 10 2004 050 308

(51) Int. Cl.
G21C 17/00 (2006.01)
G01N 1/22 (2006.01)
G21C 17/028 (2006.01)
G01N 1/10 (2006.01)

(52) U.S. Cl.
CPC ................ *G01N 1/22* (2013.01); *G21C 17/028* (2013.01); *G01N 1/2226* (2013.01); *G01N 2001/1037* (2013.01); *G21Y 2002/204* (2013.01); *G21Y 2002/304* (2013.01); *G21Y 2002/502* (2013.01); *G21Y 2004/30* (2013.01); *G21Y 2004/40* (2013.01)

(58) Field of Classification Search
CPC .................. G01N 1/22; G01N 1/2226; G01N 2001/1037; G21C 17/028; G21Y 2002/204; G21Y 2002/304; G21Y 2002/502; G21Y 2004/30; G21Y 2004/40
USPC .......................................... 376/277, 289, 293
See application file for complete search history.

(56) References Cited

U.S. PATENT DOCUMENTS

| 3,791,923 | A | * | 2/1974 | Bhan .............................. 376/300 |
| 3,890,100 | A | * | 6/1975 | Busch ............................ 436/136 |
| 4,048,012 | A | * | 9/1977 | George et al. ................. 376/298 |
| 4,092,490 | A | * | 5/1978 | Schabert et al. .............. 376/292 |
| 4,638,674 | A |   | 1/1987 | Redmann |
| 4,740,359 | A |   | 4/1988 | Hadi Ali et al. |

(Continued)

FOREIGN PATENT DOCUMENTS

| CH | 682 188 A5 | 7/1993 |
| DE | 2 309 659 | 9/1973 |

(Continued)

*Primary Examiner* — Timothy A Brainard
(74) *Attorney, Agent, or Firm* — Laurence A. Greenberg; Werner H. Stemer; Ralph E. Locher (57) ABSTRACT

A sampling system for taking a sample from the atmosphere in a reactor containment of a nuclear plant, includes a sampling line which is connected to a vacuum system and to an analysis system. The sampling line opens into the reactor containment and has a restriction device connected upstream thereof on the gas side for connection to the atmosphere in the reactor containment. A method for taking such a sample is also provided.

18 Claims, 3 Drawing Sheets

(56) References Cited

U.S. PATENT DOCUMENTS

| | | | |
|---|---|---|---|
| 5,078,960 A * | 1/1992 | Berg et al. | 376/314 |
| 5,267,282 A | 11/1993 | Labno et al. | |
| 5,272,738 A * | 12/1993 | Schegk | 376/314 |
| 5,367,546 A * | 11/1994 | Lau et al. | 376/392 |
| 5,402,454 A | 3/1995 | Eckardt | |
| 5,473,647 A * | 12/1995 | Eckardt | 376/308 |
| 5,535,253 A * | 7/1996 | Loisy et al. | 376/250 |
| 6,074,882 A * | 6/2000 | Eckardt | 436/147 |

FOREIGN PATENT DOCUMENTS

| | | |
|---|---|---|
| DE | 24 45 952 C2 | 4/1975 |
| DE | 2537393 A1 | 3/1977 |
| DE | 277 378 A3 | 4/1990 |
| DE | 41 26 894 A1 | 2/1993 |
| EP | 0 129 110 A1 | 12/1984 |
| JP | 57-4535 | 1/1982 |
| JP | 61-41994 | 2/1986 |
| JP | 10-185116 | 7/1998 |
| RU | 549725 | 3/1977 |
| RU | 2070343 C1 | 12/1996 |
| RU | 2090942 C1 | 9/1997 |
| RU | 2106028 C1 | 2/1998 |
| RU | 15023 U1 | 9/2000 |
| SU | 934340 A1 | 6/1982 |
| SU | 1170313 A1 | 7/1985 |
| SU | 1314479 A1 | 5/1987 |
| SU | 1814046 A1 | 5/1993 |

* cited by examiner

METHOD AND SAMPLING SYSTEM FOR TAKING SAMPLE FROM THE ATMOSPHERE IN THE REACTOR CONTAINMENT OF A NUCLEAR PLANT

CROSS-REFERENCE TO RELATED APPLICATIONS

This application is a continuation, under 35 U.S.C. §120, of copending International Application No. PCT/EP2005/011024, filed Oct. 13, 2005, which designated the United States; this application also claims the priority, under 35 U.S.C. §119, of German Patent Application DE 10 2004 050 308.7, filed Oct. 14, 2004; the prior applications are herewith incorporated by reference in their entirety.

BACKGROUND OF THE INVENTION

Field of the Invention

The invention relates to a sampling system for taking a sample from the atmosphere in the reactor containment of a nuclear plant. The invention also relates to a method for taking such a sample.

In a nuclear plant, in incident and in particular accident situations, significant activity release could occur after an incident involving coolant loss. In that case, hydrogen gas in particular can be formed and released inside the containment surrounding the reactor core. Then, due to the possible formation of explosive gas mixtures, the reactor containment could be at risk from uncontrolled hydrogen reactions taking place.

Various concepts are known for avoiding the formation of such explosive gas mixtures in the containment of a nuclear plant, in which the atmosphere in the reactor containment is inerted as required. In such a case, hydrogen components forming in the containment atmosphere can be ignited or burned in a controlled manner, by way of example. In that case, the hydrogen component is reduced reliably before it exceeds the ignition limit in the gas mixture above which an uncontrolled hydrogen reaction could occur. As an alternative or in addition, inert gases, such as nitrogen, can also be fed into the atmosphere of the reactor containment in a controlled manner, so that ignition of the gas mixture is impossible, just due to the high inert gas component in the containment atmosphere.

Relatively reliable determination of the respective current actual state in the containment atmosphere is necessary in order to treat such accident situations in a controlled manner in line with requirements, that is to say in order to supply inertization gases in a specific manner, for example. The containment atmosphere and its components cannot be monitored with sufficient accuracy and reliability by using directly detected actual measured values through the use of measurement or analysis systems inside the reactor containment. That is due to the relatively aggressive conditions for parts and components to be expected in the stated incident situations, as a consequence of possible high levels of radiation and/or chemical reactivity of components of the atmosphere. In order to nevertheless be in a position to appropriately consider the current actual state of the containment atmosphere as a suitable basis for controlling necessary countermeasures, a sample can also be taken, in which a small subset, also referred to as a sample, of the containment atmosphere, is taken from the reactor containment and is fed to an analysis and evaluation station disposed outside the containment. A method suitable for taking such a sample and a device suitable for carrying out the method are known, for example, from German Published, Non-Prosecuted Patent Application DE 41 26 894 A1, corresponding to U.S. Pat. No. 5,402,454.

In known sampling systems of that type, it is common to carry out measurement gas drying in an analysis cubicle disposed outside the reactor containment, with the hydrogen concentration of the dried gas subsequently being measured by using a thermal conductivity analyzer. In order to determine the true hydrogen concentration in the reactor containment from that measured value, a correction is made by using the steam content within the containment atmosphere. That correction is usually made on the assumption of saturation conditions, using the containment pressure and the containment temperature. The real steam content in the containment atmosphere and the true hydrogen concentration can only be determined with insufficient accuracy because of possible overheating. The widely varying atmosphere states from saturation conditions to the "severely overheated" state are caused by the components of active inert gases and aerosol-type fission products in the atmosphere, which can have a decay power from a few kW up to several 100 kW, depending on the accident progression. The fact that cooling effects of the structures, the external walls, cooling systems etc., can result in significant temperature fluctuations and can also be caused in the different spatial and height regions of the containment, should also be taken into account. The true atmosphere temperatures can therefore deviate from the saturation temperatures, for example by 0 to >100° C. and therefore do not allow a reliable conclusion to be drawn as to the true steam partial pressures.

As an alternative, hydrogen sensors which operate on the heat of reaction principle can also be directly inserted in reactor containments. Those sensors can be connected to a measurement electronics system disposed outside the reactor containment through the use of incident-proof, but not accident-proof, cables. Hydrogen measurement is, however, no longer possible with that measurement device alone in the case of reduced oxygen components and in particular in the case of medium-term and long-term high levels of radiation. Reliable measurement of the hydrogen concentration is thus no longer possible under inert conditions, and in that case there is also a relatively high cross-sensitivity to carbon monoxide which could be released during an interaction between concrete and a core melt. Systems of that type are therefore inadequate especially for active incident management and specific control of countermeasures.

Furthermore, only individual gas components, such as the hydrogen component or the oxygen component, can usually be analyzed in known sampling systems, in which case the inertization state of the containment atmosphere cannot be determined directly by direct measurement of the steam or carbon dioxide content.

SUMMARY OF THE INVENTION

It is accordingly an object of the invention to provide a method and a sampling system for taking a sample from the atmosphere in the reactor containment of a nuclear plant, which overcome the hereinafore-mentioned disadvantages of the heretofore-known methods and devices of this general type and with which it is possible to obtain a sample suitable for determining particularly reliable and accurate measured values for gas components of the containment atmosphere.

With the foregoing and other objects in view there is provided, in accordance with the invention, a sampling system for taking a sample from the atmosphere in a reactor containment of a nuclear plant. The sampling system comprises a sampling line opening into the reactor containment, a vacuum system connected to the sampling line and an analysis system connected to the sampling line. A restriction device is connected upstream of the sampling line on the gas side in the case of a connection to the atmosphere in the reactor containment.

The invention is based on the consideration that the sample provided should represent the atmospheric conditions inside the containment with a particularly high level of accuracy in order to determine particularly accurate measured values which are characteristic of the current actual state of the containment atmosphere. To this end, those influences which could corrupt the sample composition when compared with the true actual composition of the atmosphere in the containment, should absolutely be avoided. It has been found that the drying of the measurement gas usually carried out and the subsequent consideration of the influences of the steam content on the assumption of saturation conditions in the containment could be regarded as a possible source of such a deviation of the characteristics of the sample taken from the characteristics of the true containment atmosphere in accident situations. In the case of significant activity and hydrogen releases and the assumption of saturated steam conditions on the basis of the measured atmosphere temperatures, this easily leads to non-recognition of explosive atmosphere conditions and could cause the initiation of inappropriate countermeasures to be taken that could threaten the integrity of the containment.

In order to avoid the assumption of constraints of this type and instead to enable direct determination of the true atmosphere conditions in the containment even when overheating or other aggravating conditions may exist, condensation of any steam contained in the atmosphere, and thus also carried in the sample in the sampling line, should be reliably avoided even when passing through cooler containment regions and thus even before the measurement location for the evaluation is reached. In order to ensure this with particularly high operational reliability and passively, i.e. without the need for active control intervention from the outside, the sampling system is constructed to maintain an overheated state during transport of the sample through the sampling line. This is achieved by consistently maintaining a vacuum state in the sampling line during the transport of the sample taken. The vacuum already developed for transport reasons in the sampling line even before the actual sample is taken is also maintained during the transport of the sample in the sampling line, by appropriately restricting the sampling line in its entry region.

In accordance with another feature of the invention, in order to be able to maintain the vacuum which will exist during transport of the sample through the sampling line in a particularly simple and reliable manner, the sampling line is advantageously a small line with a nominal width of up to 15 mm and in a particularly advantageous construction a capillary line with a nominal width of about 1 to 5 mm. Such a sampling line also ensures that the volumes of the samples taken can be kept especially small, with the result that, even for relatively high amounts of activity released in the containment atmosphere, the overall activity carried into the external region of the reactor containment after taking the sample can be kept especially low. A sampling line of such dimensions furthermore also has particularly high intrinsic safety with respect to damage. That is because, even if the sampling line were to be completely torn off, the resulting additional leakage from the reactor containment into its surroundings would be negligible as compared to the leakage resulting in any case from its construction.

It is therefore possible to avoid the duplicated shut-off devices in the region of the containment penetration, including their incorporation in reactor safety systems in general, specified in conventional sampling systems due to possible larger leak cross sections. The capillary lines having a diameter of, for example, 3 mm and only 0.5 mm wall thickness, furthermore have design pressures of more than 50 bar, which fundamentally increases the safety margin against failure for containment design pressures of, for example, 5 bar. Assuming 5 to 10 samples, for example, are taken from the containment, this furthermore results in a saving of from 10 to 20 containment shut-off valves. Firstly, this leads to a significant reduction in costs and, due to valves being avoided in this region, also enables optimized sample overheating even in the passage region.

In accordance with a further feature of the invention, the restriction device may be an individual restrictor or, in order to permit a larger entry diameter, for example, also a multi-stage restrictor or else a porous body restrictor. The restriction device preferably has a free flow cross section of 0.05 to 2 mm, preferably of about 0.5 mm. In a sampling system of this construction, a pressure reduction in the sampling line to less than about 50% of the prevailing pressure in the reactor containment directly after the sample is taken is ensured by passive measures, especially in combination with the intended dimensions of the sampling line. The intended direct gas drying and overheating to the surrounding area by restriction are thus ensured in the entire region of the sampling line inside the reactor containment. Significantly more favorable conditions prevail even in the passage region through the external wall of the containment since, even at high steam partial pressures of several bar, heating of, for example 50 to 80° C. can easily be achieved, especially by additional heating through the use of a low-temperature heating element, and temperatures below the critical temperatures of, for example, concrete of approximately 80 to 100° C. can reliably be maintained.

In accordance with an added feature of the invention, the restriction device preferably additionally has a filter unit associated with it in such a way that adverse effects upon operation are ruled out even if coarse-grained impurities or the like occur. The filter unit, which can also be intended in particular for coarse aerosol retention, advantageously includes a porous filter material, such as sintered metal or braided metal fibers. The additional brief back-flushing using compressed air or nitrogen, advantageously from pressure cylinders of pressures at >10 to a cylinder pressure of, for example, 100 bar, furthermore results in any contaminated restrictor cross sections being reliably flushed free.

In accordance with an additional feature of the invention, the sample transport line outside the containment is advantageously provided with a direct heating device and the analysis system connected downstream of the sampling line advantageously has a heatable external housing in the manner of a heating cubicle in order to permit reliable evaluation of the sample taken and in particular to permit relatively accurate analysis of the entrained constituent parts of the gas. It is expediently constructed in such a way that the sample taken can be analyzed in a temperature range of about 120° C., or in the case of high positive pressures in the reactor containment of up to 160° C. This also reliably prevents the water vapor from condensing while the sample taken is evaluated, with the result that especially accurate measured values for the individual constituent parts of the gas of the containment atmosphere can be determined.

In accordance with yet another feature of the invention, particularly high operational safety and mechanical robustness of the sampling system can be achieved by advantageously laying the sampling line in a protective pipe.

In accordance with yet a further feature of the invention, the vacuum system of the sampling system is advantageously disposed outside the reactor containment in order to ensure that the number of active components inside the reactor containment can be kept especially low for reasons of particularly high operational reliability. The vacuum system which is provided may, in this case, in particular be a pump configuration disposed outside the reactor containment, for example a membrane vacuum pump or a jet pump. As an alternative or in addition, a vacuum container which can be connected by using quickly opening valves may be provided to produce fast vacuum pulses. In a multichannel construction of the sampling system, that is to say if a plurality of sampling lines are parallel-connected, a separate vacuum pump, in particular a micro vacuum pump, can also be provided for each sampling line, rather than one central pump unit.

In accordance with yet an added feature of the invention, the analysis system is preferably disposed relatively close to the reactor containment in order to keep the transport distances short. The analysis system may include, in particular, a number of adsorption columns, with separation of the constituent parts of the gas and subsequently selective measurement of the gas components using thermal conductivity detectors at the column outlet being able to be effected in different adsorption columns. Comprehensive gas analysis with respect to the content of water vapor through the use of adsorption columns through which the gas flows and also in parallel-connected adsorption columns with respect to the content of hydrogen, oxygen, carbon dioxide and/or carbon monoxide, and possibly of inert gases, is already possible, even under incident conditions, in low gas volumes of, for example, less than 1 l. In addition to the hazard potential of the containment atmosphere, specific information on a possible damaged state of the reactor core and its condition, e.g. if CO is detected, can also be obtained from these analysis values. As an alternative, or as a diverse measurement for increasing reliability, the hydrogen concentration can simply be determined in the heated cubicle by using a thermal conductivity detector, and the steam component can be determined by using capacitive polymers, in each case directly in the measurement gas. The corresponding radiation and temperature sensitive microprocessor electronics systems of the evaluation unit are disposed separately outside the heated cubicle in such a way that they are shielded.

In accordance with yet an additional feature of the invention, the system is preferably operated in such a way that the measurement sensors are flushed with inactive gases after the respective complete analysis, and the levels of radiation are thus significantly reduced with respect to continuous analysis, even in the analyzer region. The system and the devices are advantageously controlled by using freely programmable digital control measures such that, for example depending on the real installation situation in the plant, taking into account the different transport times, the corresponding vacuum pulses can be matched in situ by changing the parameters. High quality insulation of <100 W/m$^2$ minimizes the thermal losses in the region of the pipeline and cubicle to <5 kW continuous power, with the result that the electric supply can be ensured, even in the event of power cuts or failures, expediently through a battery network or separate standby diesel generators, in such a way that they can be permanently or quickly switched in.

In accordance with still another feature of the invention, in order to permit the sample taken to be fed in a required manner to the analysis system, a sample insulation container is preferably connected in the sampling line before entry or upon entry into the analysis system. A buffer container or pipeline buffer, having a volume which is larger than the volume of the sample insulation container by about a factor of from 2 to 10 in an expedient refinement, can furthermore be connected upstream of the sample insulation container. This measure ensures that no changed measurement gas can be transported into the measurement gas volume (sample insulation container) after the loss-free vacuum operational phase of the sampling lines to the containment passage in the subsequent pressure build-up phase by a drop below the dew point which is then possible in the capillary line inside the containment. These segments are then dried by subsequent back-flushing with dry gas, e.g. nitrogen, before the next sample is taken. As an alternative, the measurement gas compression can also be initiated by feeding in gas, in which case, once again, addition of changed measurement gas into the sample preparation container is avoided due to the upstream volume and the plug flow which occurs in the case of small pipeline dimensions.

In accordance with still a further feature of the invention, in order to ensure that the overheating of the sample taken during its transport through the sampling line is kept up as planned, the sampling line is advantageously constructed in such a way that it can be heated in the region outside the reactor containment. This ensures that, if required, water vapor is prevented from condensing even over relatively long transport distances by specific heating of individual regions of the sampling line, without active components having to be fitted inside the reactor containment.

In accordance with still an added feature of the invention, in order to keep the activities possibly released into the external region while the sample is being taken especially low, a further advantageous refinement provides that a return line opening into the reactor containment is connected to the sampling line. In this case, the extracted activities can in particular be returned through the use of a compressor unit and/or by providing an inert gas delay line, for example on an active carbon or zeolite basis. This can be achieved by particularly simple measures, preferably by using a gas jet or at least temporarily by compressed gas taken from gas cylinders to carry out the conveyance and to produce a vacuum.

With the objects of the invention in view, there is also provided a method for taking a sample from the atmosphere in a reactor containment of a nuclear plant. The method comprises producing a vacuum in a sampling line, relative to a pressure prevailing in the reactor containment, and limiting the pressure in the sampling line to a maximum of about 60% of the pressure in the reactor containment after an inflow of a sample into the sampling line.

In accordance with another mode of the invention, this is advantageously ensured by restricting the inflow of the sample into the sampling line and/or the inflow of components of the atmosphere into the sampling line.

The described concept for taking a sample and subsequent analysis works substantially independently of the current oxygen concentration in the reactor containment, with respect to the accuracy and reliability which can be achieved. In accordance with a further mode of the invention, a further increase in the reliability and thus in the operational safety can advantageously be achieved by combining this method with a "heat of reaction" method for measuring the hydrogen concentration in the reactor containment. This method works as a function of the oxygen concentration.

In this case, the hydrogen concentration is preferably additionally measured at a number of points or locations in the reactor containment in the manner of diverse redundancy, using the heat of reaction principle. The measurement locations for the two methods intended for this purpose are advantageously disposed in the same spatial regions of the reactor containment, so that the fuel gas concentration, the oxygen concentration and the true hydrogen concentration can be comparatively accurately determined, especially in the early phase of a possible accident sequence, by comparing the measured values obtained from the two methods with one another.

In the heat of reaction method, a catalytically active and a catalytically inactive heated filament are accommodated in a sensor head which is fitted directly in the atmosphere of the reactor containment. If hydrogen is present in the surrounding atmosphere, oxidation takes place, depending on the respective oxygen concentration, on the catalytically active filament which is connected through cables to an electronics system disposed outside the reactor containment. The electrical resistance change resulting therefrom on the basis of the temperature increase taking place is electrically compensated for through the use of a bridge circuit. The compensation current is a direct measure of the hydrogen oxidation that has taken place and can be output as a hydrogen measurement signal or fuel gas concentration.

The signals produced in the process are expediently additionally conditioned in a control and evaluation unit used by both analysis methods.

The hydrogen concentration determined by measurement by using the above-described method by thermal conductivity corresponds to the true concentration, independently of the current oxygen concentration. Thus, the actual hydrogen concentration (thermal conductivity) and, (if excess oxygen is present when using the heat of reaction) the hydrogen concentration, can be determined in a redundant form by comparing the hydrogen concentration values determined by using both methods.

In the probable cases of relatively high hydrogen concentrations with simultaneous reduced oxygen concentrations, which are relevant for safety purposes in possible accident situations, it is possible to determine the maximum hydrogen concentration by using the thermal conductivity principle, the fuel gas concentration by using the sensor heat of reaction method and additionally the oxygen concentration.

In addition, the hydrogen release rates and, on the basis of the defined amount of oxygen in the reactor containment, also the hydrogen oxidation rates, can be determined and balanced by using a suitable computer circuit to monitor the measured values obtained by the sampling analysis and permanently comparing them with the measured values from the sensor/cable method. This enables important conclusions to be drawn in terms of not only a current hazard potential for the plant, but also in particular in terms of the incident progression, for example whether the fuel rod oxidation could be stopped, so that appropriate countermeasures can be initiated in a specific manner.

The methods mentioned are used advantageously in particular in the transient early accident phase, since in the further accident progression the oxygen in the containment undergoes a reaction. Advantageously in terms of the manufacturing and installation complexity, the cables of the sensor/cable method can therefore be in the form of plastic cables without a fully ceramic cable construction, with a structure having a functional life under medium exposure to radiation of up to 24 h being regarded as sufficient. As the accident progresses, a cable failure is tolerated due to the progressively high levels of radiation in the reactor containment and is likewise recognized by the electronic system, with the result that subsequently only the sampling and analysis method is used in the measurement.

The advantage achieved by the invention is in particular that an overheated state of the sample taken can be consistently maintained even during the transport of the sample from the extraction point to the analysis system disposed outside the reactor containment, by setting a suitably selected vacuum in the sampling line and maintaining it by restriction as the sample flows into the sampling line. The condensation of water vapor, leading to possible corruption of analysis results, during the transport of the extracted sample, is therefore precluded. The sample can thus be analyzed in a state in which it particularly accurately represents the true conditions inside the reactor containment. Especially reliable measurement results with respect to the current actual state of the containment atmosphere can be determined without the need to resort to generalizing data or estimated values. The particularly accurate actual value determination for the containment atmosphere which can thus be achieved enables management and control of countermeasures, which are particularly in line with requirements, and thus particularly reliable operational management for incident management as well.

In addition, suitably selecting the dimensions of the sampling line and of the further components keeps the extraction of activity taking place while the sample is being taken particularly low even in relatively serious accident situations, such that an activity release to the surrounding area can be kept especially low. Good quality insulation of <100 W/m$^2$ minimizes the thermal losses in the region of the pipeline and cubicle to <5 kW continuous power, with the result that the electrical supply, even in "station black" situations, can be ensured expediently through a battery network or separate emergency diesel generators, permanently or for short periods. In the early phase of a possible accident progression, a permanent hydrogen concentration measurement can be achieved by expediently combining hydrogen sensors additionally fitted in the reactor containment and the method described herein. In this case, the hydrogen concentration at a few points in the reactor containment is additionally measured by using the heat of reaction principle. In this case, a catalytically active and a catalytically inactive heated filament are accommodated in the sensor head. When hydrogen collects, the oxidation takes place on the catalytically active filament which is connected through cables to an electronic system disposed outside the reactor containment. The resulting electrical resistance change is electrically compensated for through the use of a bridge circuit. The signals produced are additionally conditioned in a control and evaluation unit used by both methods. Thus a permanent hydrogen signal can be produced quickly and a statement about the oxygen content in the atmosphere can be obtained as soon as the existing analysis and the hydrogen measured value obtained by thermal conductivity are available.

The monitoring of the measured values obtained and the comparison with sensor/cable methods can be used to additionally monitor the time of failure on the grounds of the extreme high levels of radiation in the cable region.

Other features which are considered as characteristic for the invention are set forth in the appended claims.

Although the invention is illustrated and described herein as embodied in a method and a sampling system for taking a sample from the atmosphere in the reactor containment of a nuclear plant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
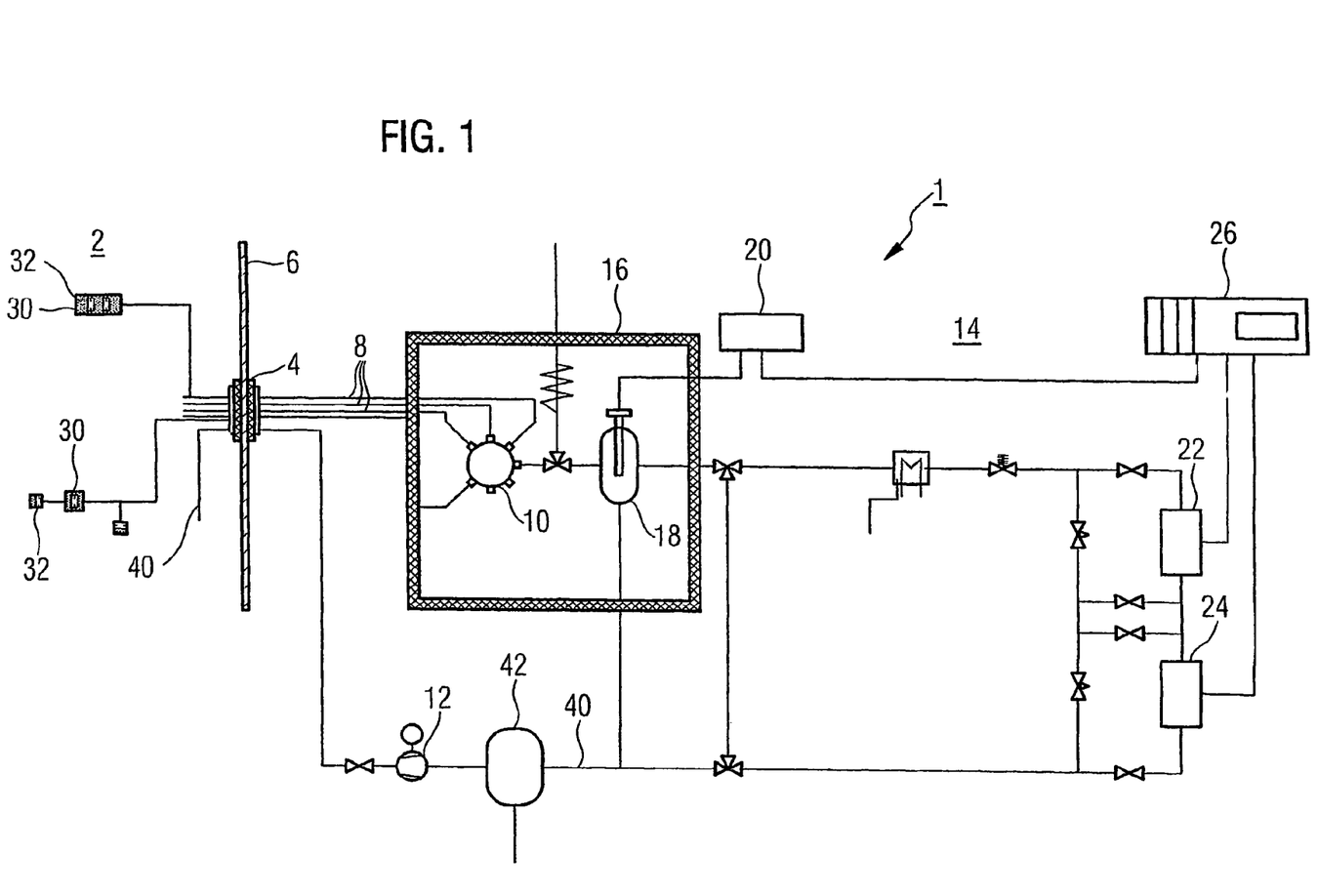
FIG. 1 is a schematic and diagrammatic view of a sampling system.

Referring now in detail to the figures of the drawings, in which identical elements are provided with the same reference symbols, and first, particularly, to FIG. 1 thereof, there is seen a sampling system 1 which is intended for taking a sample from the atmosphere in a reactor containment 2 of a non-illustrated nuclear plant. To this end, the sampling system 1 includes a plurality of sampling lines 8 which open into the reactor containment 2 and are passed through an external wall 6 thereof through a passage 4. These sampling lines 8 are connected to a vacuum system 12 and to an analysis system 14 through a valve block 10 which can be used to selectively and specifically choose any desired sampling line 8. The analysis system 14 includes an external housing 16 which is constructed to be heatable in the manner of a heating cubicle. Besides the valve block 10, a sheathed or clad gas analyzer 18 is also disposed in the external housing 16. The gas analyzer 18 is in the form of a capacitive sensor, for example, and is connected to a first measurement electronics system or measurement location 20 for determining the water vapor content, to a second measurement location 22 for determining a hydrogen component, preferably using the thermal conductivity principle, and to a third measurement location 24 for determining an oxygen component. The measurement locations 20, 22, 24 are connected on the output side to a central evaluation electronics unit 26, which also assumes complete system control and possibly comparison with diverse sensor signals. In one variant, which is not illustrated, the cooler can be dispensed with and the measurement locations 22 and 24 can also be disposed in the heating cubicle 16.

The sampling system 1 is constructed for obtaining especially accurate and reliable measurement results for the gas components in the atmosphere inside the containment 2. For this purpose, condensation of entrained water vapor is intended to be avoided in a specific manner during the transfer of the sample from the interior of the reactor containment 2 to the gas analyzer or separator 18 in such a way that the entrained water vapor can be detected and taken into consideration, qualitatively as well as quantitatively, in the subsequent evaluation. In order to achieve this, the sampling system 1 is constructed to transfer the sample in the overheated state to the gas analyzer or separator 18 of the analysis system 14. The overheated state is set and maintained by passive measures, that is to say without the need for active intervention from the outside, by setting and maintaining a suitably selected underpressure, vacuum or negative pressure during the transport of the sample in the sampling line 8. For this purpose, the sampling lines 8 each have a restriction device 30 at their end which opens into the reactor containment 2.

The restriction device 30, which has a filter 32, for example made of a porous filter material such as sintered metal or braided metal fibers, connected upstream thereof, for avoiding blocking as well as for coarse aerosol retention, is specifically constructed to maintain a vacuum or underpressure, in particular of less than about 50% of the containment pressure in the respective sampling line 8, even when atmosphere flows in from the internal space of the reactor containment 2. In order to achieve this by relatively simple measures, firstly, the respective sampling line 8 is a capillary line with a relatively small nominal width of about 3 mm and secondly the restriction device 30, which is connected upstream in each case, is appropriately dimensioned and constructed with a free flow cross section of about 0.5 mm. The sample is transported, based on the high vacuum in the capillary lines, preferably at >5 m/s to 50 m/s, with the result that low transport speeds can be achieved.

The sampling lines 8 are additionally constructed to be heatable in the region outside the external wall 6 of the reactor containment 2. The passage through the reactor containment is heated by using low temperature elements to <80° C. This ensures the maintenance of the overheated state of the sample taken until it arrives in the analysis system 14, even in the case of a relatively long line.

In order to return activities, which may have been taken at the same time as the sample, into the interior of the reactor containment 2, each sampling line 8 is connected to a return line 40 opening into the reactor containment 2. The return line 40, into which a return conveyance container 42 is connected for buffering as required, is provided with a vacuum pump, provided as the vacuum system 12, in such a way that it can also be used, in addition to the evacuation of the respective sampling line 8, for return conveyance to the reactor containment 2.

Figure 2:
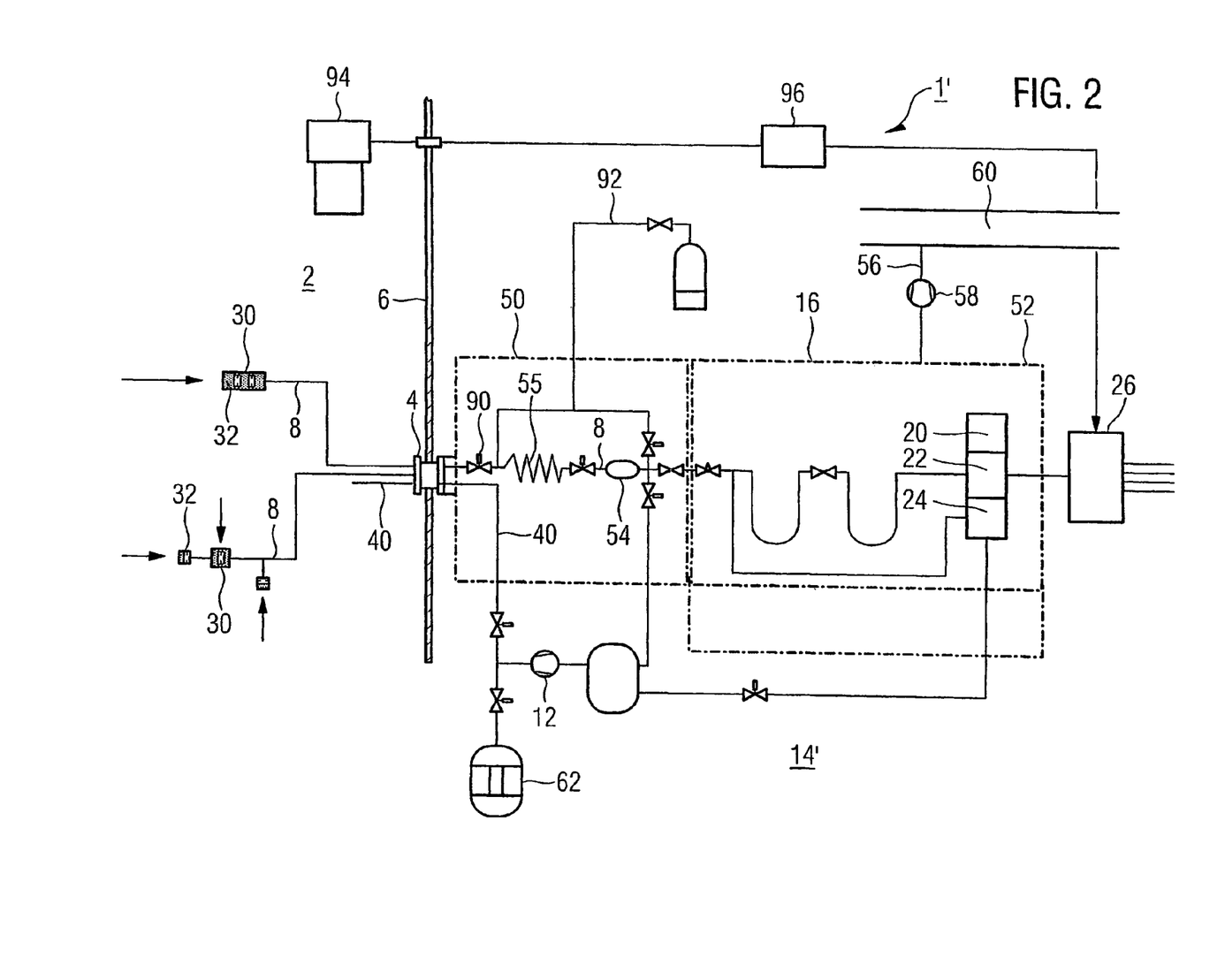
FIG. 2 is a schematic and diagrammatic view of an alternative embodiment of a sampling system.

In the exemplary embodiment shown in FIG. 2, a sampling system 1' has an analysis system 14', which is substantially of modular construction. The analysis system 14' includes a sampling module 50 and a measurement module 52 which is disposed in the heatable external housing 16 that is in the form of a heating cubicle. In this exemplary embodiment, a sample insulation container 54 is disposed in the sampling module 50. In the insulation container 54, the sample taken from the internal space of the reactor containment 2 through a sampling line 8 can be temporarily stored, directly analyzed or held ready for subsequent evaluation. The sampling module 50 furthermore includes any required measurement probes, micro multiport valves, micro shut-off valves, fast opening vacuum valves and restrictors or throttles and/or pressure reducing valves.

An additional volume 55 connected upstream of the sample insulation container 54 in the sampling line 8 can ensure that altered or changed measurement gas cannot be transported into the measurement gas volume after the vacuum operation in the subsequent pressure build-up phase by a drop below the dew point which is then possible in the capillary line inside the reactor containment 2. As an alternative, a pressure build-up in the sample insulation container 54 can be achieved by the same method without measurement gas corruption by closing a valve 90, which is connected in the sampling line 8, and by a pressure build-up through a gas feed 92 and by gas flowing through the additional volume 55. This back-flushing with dry gas, e.g. nitrogen, dries these segments before the next sample is taken. As an alternative, the measurement gas compression can also be initiated through the gas feed 92 and by closing the valve 90, in which case, once again, addition of altered or changed measurement gas into the sample preparation container is avoided due to the additional volume 55 which is connected upstream and of a plug flow in the pipeline.

The additional volume 55 can, in particular, also serve as a buffering volume and is larger than the internal volume of the sample insulation container 54 by a factor of about from two to five.

Sample metering components and adsorption columns necessary for the actual measurement and the measurement locations and sensors 20, 22, 24 are included in the measurement module 52 connected downstream. The measurement module 52 is connected to an exhaust air system 60 through a discharge line 56, into which a vacuum fan 58 is connected.

The return line 40 is additionally connected in the sampling system 1 to an inert gas delay section 62, in particular on an active carbon or zeolite basis, to ensure an activity release which is kept particularly low. As is also shown in FIG. 2, a hydrogen measurement is also provided in combination with or as a redundant measure to the sampling system. The measurement involves a number of hydrogen sensors 94, which are disposed in the reactor containment 2 and are connected on a data side to a shared evaluation unit 96 disposed outside the reactor containment 2. Signals obtained in this evaluation unit 96 are additionally fed to the control and evaluation electronics unit 26 used by both methods.

Figure 3:
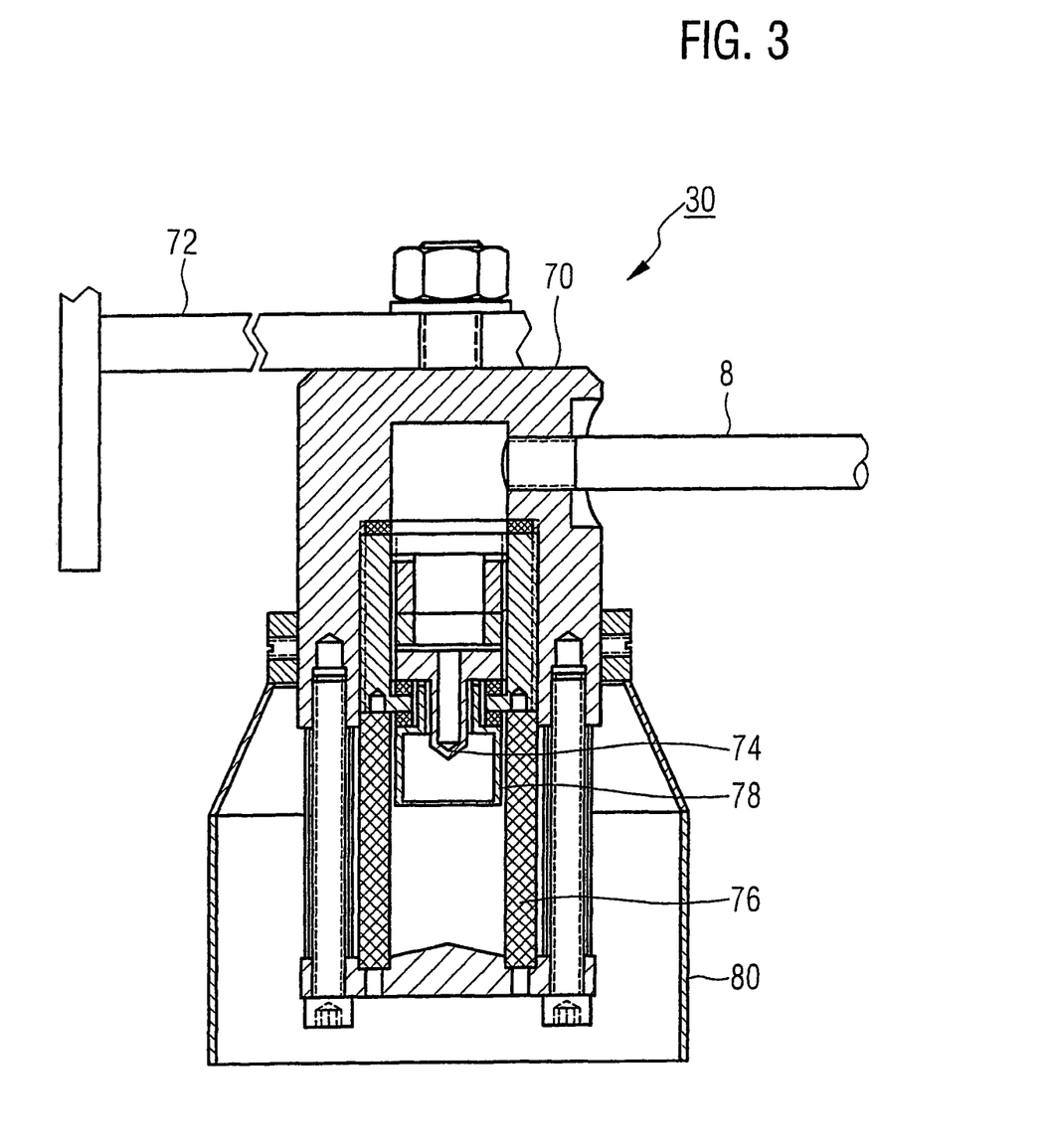
FIG. 3 is an enlarged, fragmentary, sectional view of a restriction device for application in a sampling system according to FIG. 1 or FIG. 2.

FIG. 3 illustrates an enlarged cross section through one exemplary embodiment of the restriction device 30 connected upstream of a respective sampling line. The restriction device 30 includes a base body 70 which is attached to a wall element of the reactor containment 2 through an appropriately dimensioned and selected wall holder 72. The base body 70 is furthermore connected to an opening end of the sampling line 8.

The restriction device 30 includes a restrictor or throttle element 74, which has a small free flow cross section of about 0.5 mm in comparison to the nominal width of the sampling line 8 of about 3 mm in the form of a capillary line, for ensuring that atmosphere gas flows into the sampling line 8 in a restricted manner. The inflow region of the restrictor element 74 is surrounded by a substantially cylindrical droplet or solids separator 76 in the manner of a coarse demister. A filter body 78 made of sintered metal or braided metal fibers is disposed inside the separator 76 to form a filter device. The configuration formed by these components is surrounded by a cladding or sheathing 80 intended as spray protection.

We claim:

1. A combination of a reactor containment of a nuclear plant and a sampling system for taking a sample from an atmosphere in the reactor containment of the nuclear plant, the sampling system comprising:
   a sampling line having an end opening into the reactor containment;
   a vacuum system connected to said sampling line;
   an analysis system connected to said sampling line; and
   a restriction device including a throttle located in the reactor containment at said end of said sampling line for connection to the atmosphere in the reactor containment, said restriction device configured to preclude condensation of the sample by maintaining a vacuum state while the sample is transported from said restriction device to said analysis system in said sampling line;
   wherein said sampling line is a capillary line with a nominal width of about 1 to 5 mm, and said restriction device has a free flow cross section of 0.05 to 2 mm.

2. The combination according to claim 1, wherein said restriction device has a free flow cross section of about 0.5 mm.

3. The combination according to claim 1, which further comprises a filter unit associated with said restriction device.

4. The combination according to claim 1, wherein said analysis system has a heatable external housing.

5. The combination according to claim 1, which further comprises external insulation limiting thermal losses to less than 100 W/m$^2$.

6. The combination according to claim 1, which further comprises external insulation limiting thermal losses to less than 50 W/m$^2$.

7. The combination according to claim 1, which further comprises an associated freely programmable digital control unit for open-loop and closed-loop control.

8. The combination according to claim 1, which further comprises a protective pipe in which said sampling line is laid.

9. The combination according to claim 1, wherein said vacuum system is disposed outside the reactor containment.

10. The combination according to claim 1, which further comprises a sample insulation container connected in said sampling line upstream of said analysis system.

11. The combination according to claim 10, which further comprises a buffer volume connected upstream of said sample insulation container, said sample insulation container having an internal volume being smaller than said buffer volume by a factor of from two to five.

12. The combination according to claim 1, wherein said sampling line is heatable in a region outside the reactor containment.

13. The combination according to claim 1, wherein said analysis system includes at least one of a number of capacitive polymer sensors or thermal conductivity detectors, for gas analysis of at least one of constituent parts of hydrogen or steam content or carbon monoxide.

14. The combination according to claim 1, which further comprises a return line connected to said sampling line and opening into the reactor containment.

15. The combination according to claim 1, which further comprises:
   a number of hydrogen sensors constructed according to the heat of reaction principle and disposed inside the reactor containment;
   an external evaluation unit connected on a data side to said hydrogen sensors; and
   a shared evaluation electronics unit connected to said external evaluation unit.

16. The combination according to claim 1, wherein said restriction device sets and maintains the sample in an overheated state while the sample is in said sampling line and is transported to said analysis system.

17. The combination according to claim 1, wherein said restriction device is located in the reactor containment.

18. A combination of a reactor containment of a nuclear plant and a sampling system for taking a sample from an atmosphere in the reactor containment of the nuclear plant, the sampling system comprising:
   a sampling line having an end opening into the reactor containment;
   a vacuum system connected to said sampling line;
   an analysis system connected to said sampling line; and
   a restriction device including a throttle located in the reactor containment at said end of said sampling line for connection to the atmosphere in the reactor containment, said restriction device configured to preclude condensation of the sample by maintaining a vacuum state while the sample is transported from said restriction device to said analysis system in said sampling line;

wherein said sampling line is a capillary line with a nominal width of about 1 to 5 mm, and said restriction device has a free flow cross section of 0.05 to 2 mm; and wherein no fuel gas is admixed to the sample prior to transporting the sample.

* * * * *